United States Patent [19]

Walker et al.

[11] 4,401,599

[45] Aug. 30, 1983

[54] PREPARATION OF 21-HALO STEROIDS

[75] Inventors: Jerry A. Walker; Edward J. Hessler, both of Kalamazoo, Mich.

[73] Assignee: The Upjohn Company, Kalamazoo, Mich.

[21] Appl. No.: 378,941

[22] Filed: May 17, 1982

Related U.S. Application Data

[62] Division of Ser. No. 264,593, May 18, 1981, Pat. No. 4,357,279.

[51] Int. Cl.³ ............................................. C07J 5/00
[52] U.S. Cl. ........................... 260/397.45; 260/239.5; 260/397.5
[58] Field of Search .................................. 260/397.45

[56] References Cited

U.S. PATENT DOCUMENTS 4,041,055  8/1977  Shephard et al. ............... 260/397.3
4,336,200  6/1982  Ayer et al. ..................... 260/397.45
4,342,702  8/1982  Walker et al. .................. 260/397.3

OTHER PUBLICATIONS

J. Am. Chem. Soc. 86, 3840, (1964).
J. Org. Chem. 35, 2831, (1970).

*Primary Examiner*—Elbert L. Roberts
*Attorney, Agent, or Firm*—Bruce Stein

[57] ABSTRACT

A process for the preparation of corticoids (XI) which comprises reacting a protected 17-keto steroid (II) with a metallated 1,2-dihaloethene (III).

31 Claims, No Drawings

PREPARATION OF 21-HALO STEROIDS

This is a division of application Ser. No. 264,593, filed May 18, 1981 now U.S. Pat. No. 4,357,279.

BACKGROUND OF THE INVENTION

In the past few years, 17-keto steroids have become much more readily available as starting materials for corticoid synthesis because of the discovery of a number of microorganisms which will cleave the $C_{17}$ side chain of various steroid substrates, see U.S. Pat. Nos. 4,035,236, 3,684,657 and 3,759,791.

U.S. Pat. No. 4,041,055 claims a process for producing 17α-hydroxyprogesterone and corticoids from 17-keto steroids. The first step is addition of a 2-carbon moiety by formation of ethisterone. This is followed (1) by reaction with phenylsulfenyl chloride to form an allene sulfoxide, (2) Michael addition to form a sulfoxide, (3) reaction with a thiophile and (4) reaction with a peracid to give the 17α,21-dihydroxy-20-keto corticoid side-chain.

U.S. Pat. No. 4,216,159 claims a process of transforming a 17-keto steroid to the corresponding 16-unsaturated-21-hydroxy-20-keto steroid by reaction with a lithiated chlorovinyl ether. The objective of that patent is to provide $\Delta^{16}$-$C_{21}$ steroids which can then be used to make $C_{16}$ functionalized corticoids.

The process of the present invention does not involve lithiated chloro vinyl ethers and does not produce $\Delta^{16}$-$C_{21}$ steroids.

The process of the present invention is similar to the process of U.S. Pat. No. 4,041,055 in that it transforms a 17-keto steroid to the corresponding corticoid, but does so by a different synthetic pathway.

The base catalyzed isomerization of β, γ to α,β-unsaturated sulfoxides is well known, see J. Am. Chem. Soc. 86, 3840 (1964) and the addition of nucleophiles to β-halo-α,β-unsaturated sulfoxides has been previously observed in simple systems, see J. Org. Chem. 35, 2831 (1970).

The present invention relates to a process for the preparation of 21-halo steroids useful in the preparation of pharmaceutically useful corticoids for which the essential material constituting a disclosure thereof is incorporated here by reference from U.S. patent application Ser. No. 264,593, filed May 18, 1981, now U.S. Pat. No. 4,357,279.

We claim:

1. A process for the preparation of a 21-halo steroid of the formula

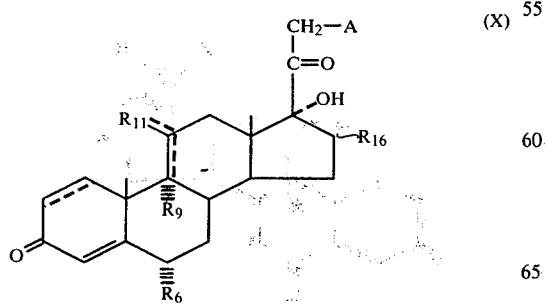

(X)

which comprises (1) contacting a protected 17-keto steroid selected from the group consisting of compounds of the formula

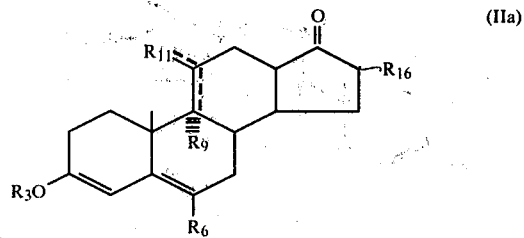

(IIa)

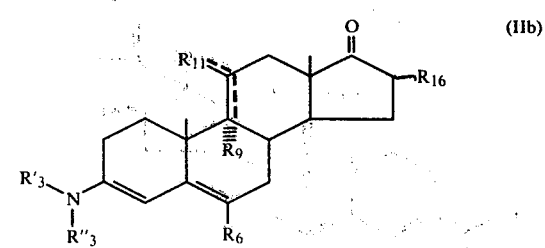

(IIb)

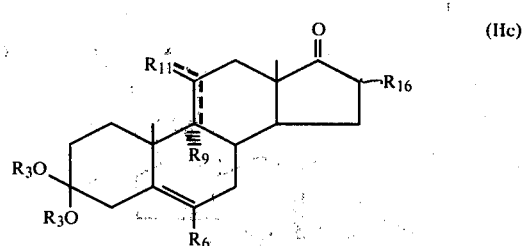

(IIc)

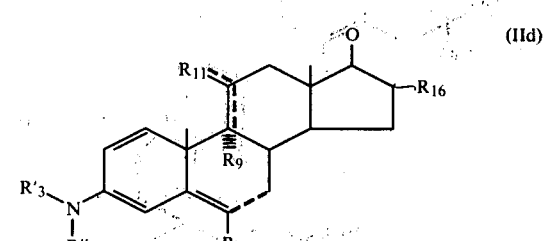

(IId)

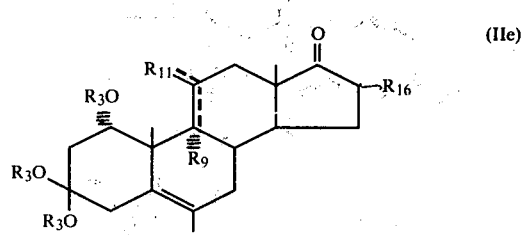

(IIe)

with a metallated 1,2-dihalogenated ethene of the formula

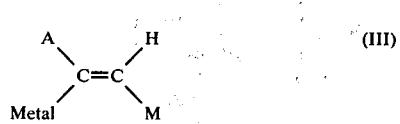

(III)

to form the corresponding protected $C_{21}$-steroid selected from the group consisting of compounds of the formula

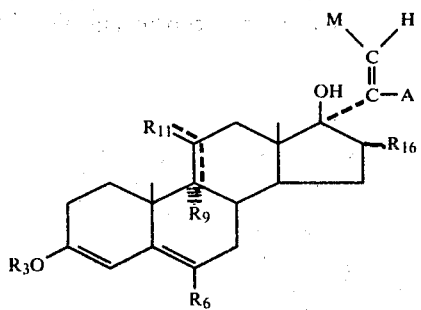 (IVa)

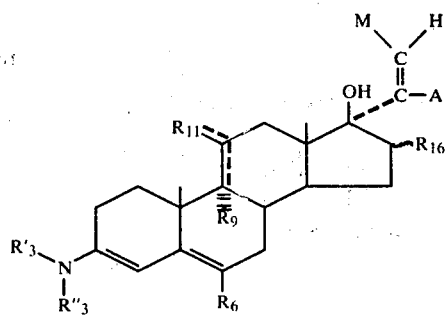 (IVb)

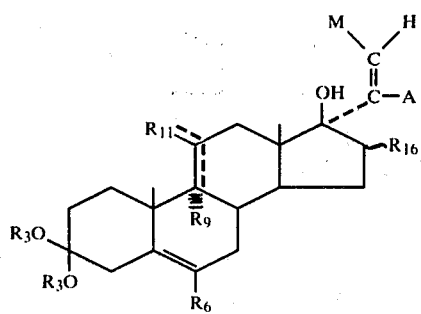 (IVc)

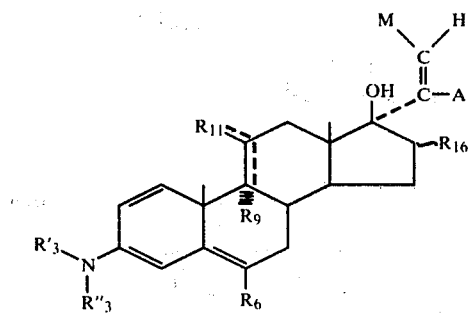 (IVd)

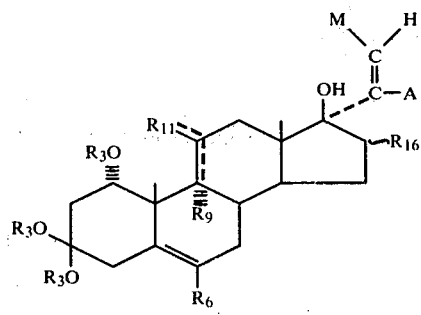 (IVe)

respectively;

(2) hydrolyzing the protected $C_{21}$-steroids (IVa–IVe) with acid to remove the protecting group and give a $C_{21}$-steroid of the formula

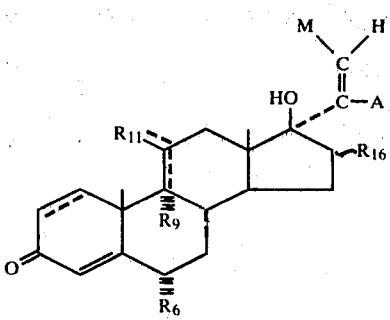 (V)

(3) contacting the $C_{21}$-steroid (V) with a sulfenylating agent of the formula $R_{22}$—S—X (VI) to give a 20,21-dihalo steroid of the formula

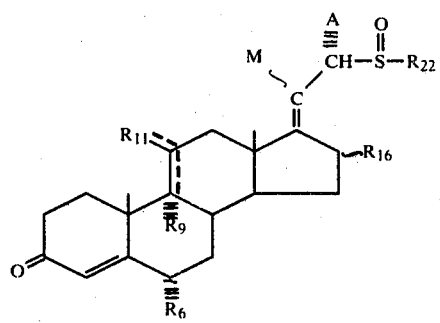 (VII)

(4) contacting the 20,21-dihalo steroid (VII) with an alkoxide, or mercaptide of the formula $OR_{20}^{\ominus}$ or $SR_{20}^{\ominus}$, respectively, to give a sulfoxide of the formula

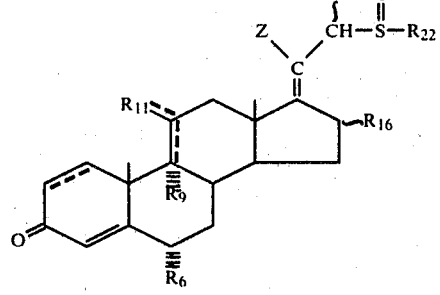 (VIII)

(5) contacting the sulfoxide (VIII) with a thiophile to give a 20-unsaturated steroid of the formula

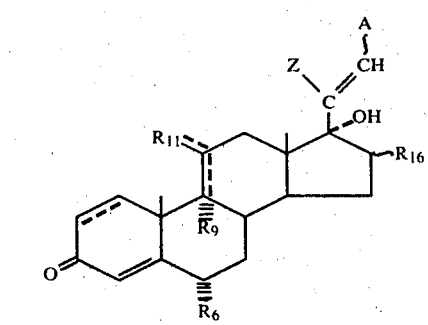 (IX)

and (6) hydrolyzing the 20,21-unsaturated steroid (IX) with acid where
A is a fluorine, chlorine or bromine atom,
M is a fluorine, chlorine or bromine atom,
$R_3$ is alkyl of 1 thru 5 carbon atoms with the proviso that with the ketal (IIIc and IIIe), the $R_3$ groups can be connected to form the ethylene ketal,
$R_3'$ is alkyl of 1 thru 5 carbon atoms,
$R_3''$ is alkyl of 1 thru 5 carbon atoms,
$R_6$ is a hydrogen or fluorine atom or methyl group,
$R_9$ is a hydrogen or fluorine atom, hydroxyl group, $-OSi(R)_3$ or nothing,
$R_{11}$ is (H), (H,H), (H, β-OH), (H, β-OSi(R)$_3$), or O,
$R_{16}$ is a hydrogen atom or methyl group,
$R_{20}$ is alkyl of 1 thru 4 carbon atoms or phenyl,
$R_{22}$ is alkyl of 1 thru 5 carbon atoms, trichloromethyl, phenyl, phenyl substituted with 1–4 carbon atoms or substituted with 1 thru 3 nitro or trifluoromethyl groups, aralkyl of 7 thru 12 carbon atoms or $-N-(R_{122})_2$ or phthalamide,
X is a chlorine or bromine atom, phenylsulfone, phthalimide or imidazole group,
Z is $-OR_{20}$ or $-SR_{20}$,
metal is lithium, sodium or potassium,
~ indicates the attached group can be in either the α or β configuration, and
... is a single or double bond.

2. A process according to claim 1, where for the 21-halo steroid (X), $R_6$ and $R_{16}$ are hydrogen atoms, where $R_9$ is nothing and $R_{11}$ is [H] which gives a $\Delta^{9,11}$ functionality in the C ring.

3. A process according to claim 1, where the temperature for the coupling reaction is from about $-120°$ to about $-20°$.

4. A process according to claim 1, where the coupling reaction is performed in a dry solvent.

5. A process according to claim 1, where the metallated 1,2-dihalogenated ethene (III) is selected from the group consisting of lithiated trans-1,2-dichloroethene, lithiated trans-1,2-chlorofluoroethene, lithiated trans-1,2-dibromoethene, lithiated trans-1,2-difluoroethene and lithiated trans-1,2-bromofluoroethene.

6. A process according to claim 5 where the metallated 1,2-dihalogenated ethene (III) is lithiated trans-1,2-dichloroethene.

7. A process according to claim 1, where the acid to remove the $C_3$ protecting group is present in a catalytic amount.

8. A process according to claim 1, where the acid to remove the $C_3$ protecting group is selected from the group consisting of p-TSA, hydrochloric acid, sulfuric acid, and phosphoric acid.

9. A process according to claim 1 where for the sulfenylating agent, $R_{22}-S-X$, X is a chlorine or bromine atom, and $R_{22}$ is a phenyl group.

10. A process according to claim 1 where the temperature range for the sulfenylating reaction is from about $-80°$ to about $25°$.

11. A process according to claim 1, where the base is an alkoxide.

12. A process according to claim 11 where the alkoxide is methoxide or phenoxide.

13. A process according to claim 1, where the reaction with base is performed in a polar solvent.

14. A process according to claim 1, where 1.5–2.0 equivalents of base are used.

15. A process according to claim 1 where the thiophile is selected from the group consisting of acetone, 3-pentanone, cyclohexanone, 1-(phenylthio)acetone, 2,4-pentanedione, trimethylphosphite, mesityl oxide, dimethyl malolate, 2,6-di-t-butylphenol, ethylvinyl ether, and dihydropyran.

16. A process according to claim 1 where the thiophile is a ketone.

17. A process according to claim 16 where the ketone is acetone.

18. A process according to claim 1 where the acid for hydrolyzing the 20-unsaturated steroid (IX) is p-TSA, hydrochloric acid, sulfuric acid, or phosphoric acid.

19. A process for the preparation of a 21-halo steroid of the formula

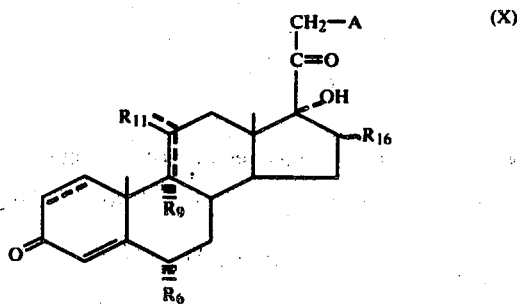

which comprises hydrolyzing a 20-unsaturated steroid of the formula

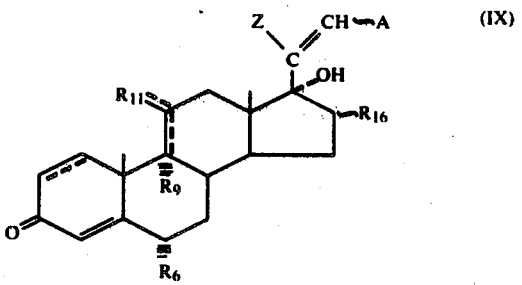

with acid where A, $R_6$, $R_9$, $R_{11}$, $R_{16}$, Z, ~ and ... are defined in claim 7.

20. A process according to claim 19, where for the 21-halo steroid (X), $R_6$ and $R_{16}$ are hydrogen atoms, where $R_9$ is nothing and $R_{11}$ is [H] which gives a $\Delta^{9,11}$ functionality in the C ring.

21. A process according to claim 19, where the aqueous acid for hydrolyzing the 20-unsaturated steroid (IX) is p-TSA, hydrochloric acid, sulfuric acid, or phosphoric acid.

22. A process for the preparation of a 21-halo steroid of the formula

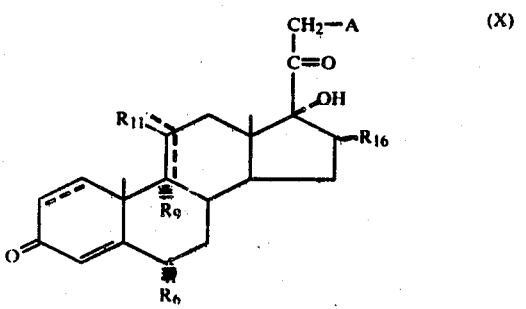

which comprises (1) contacting a 20,21-dihalo steroid of the formula

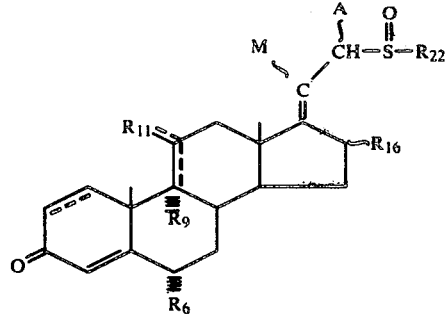

(VII)

with an alkoxide or mercaptide of the formula $OR_{20}^{\ominus}$ or $SR_{20}^{\ominus}$, respectively, to give a sulfoxide of the formula

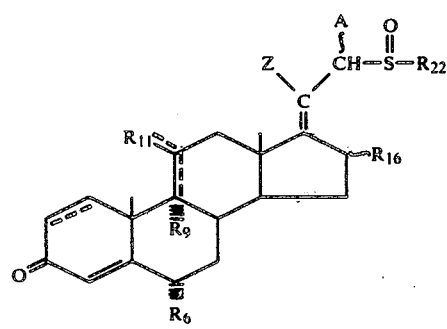

(VIII)

(2) contacting the 20-halo steroid (VIII) with a thiophile to give a 20-unsaturated steroid of the formula

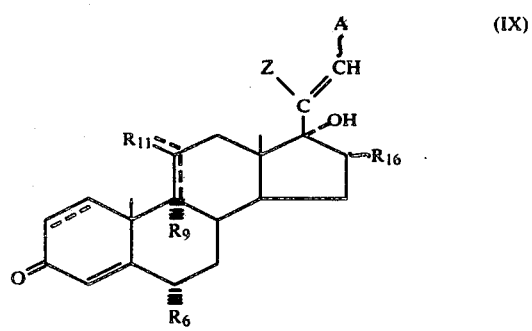

(IX)

and (3) hydrolyzing the 20-unsaturated steroid (IX) with acid where A, M, $R_6$, $R_9$, $R_{11}$, $R_{16}$, $R_{20}$, $R_{22}$, Z, ~, and . . . are defined in claim 1.

23. A process according to claim 22, where for the 21-halo steroid (X), $R_6$ and $R_{16}$ are hydrogen atoms, where $R_9$ is nothing and $R_{11}$ is [H] which gives a $\Delta^{9,11}$ functionality in the C ring.

24. A process according to claim 22, where the base is an alkoxide.

25. A process according to claim 24 where the alkoxide is methoxide or phenoxide.

26. A process according to claim 22, where the reaction with base is performed in a polar solvent.

27. A process according to claim 22, where 1.5–2.0 equivalents of base are used.

28. A process according to claim 22, where the thiophile is selected from the group consisting of acetone, 3-pentanone, cyclohexanone, 1-(phenylthio)acetone, 2,4-pentanedione, trimethylphosphite, mesityl oxide, dimethyl malonate, 2,6-di-t-butylphenol, ethylvinyl ether, and dihydropyran.

29. A process according to claim 22, where the thiophile is a ketone.

30. A process according to claim 29, where the ketone is acetone.

31. A process according to claim 22, where the aqueous acid for hydrolyzing the 20-unsaturated steroid (IX) is p-TSA, hydrochloric acid, sulfuric acid, or phosphoric acid.

* * * * *

UNITED STATES PATENT OFFICE
CERTIFICATE OF CORRECTION

Patent No. 4,401,599  Dated August 30, 1983

Inventor(s) Jerry A. Walker et al.

It is certified that error appears in the above-identified patent and that said Letters Patent are hereby corrected as shown below:

Column 1, line 60; column 6, line 20; column 6, line 60, in formula (X) the side chain at $C_{17}$ should appear as follows:

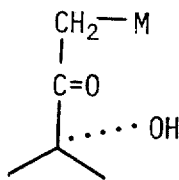

Column 4, line 25, column 7, line 10, in formula (VII) the side chain at $C_{17}$ should appear as follows:

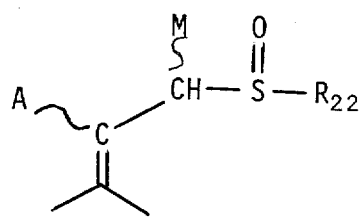

UNITED STATES PATENT OFFICE
CERTIFICATE OF CORRECTION

Patent No. 4,401,599　　　　　　　　　　Dated　August 30, 1983

Inventor(s)　Jerry A. Walker et al.

It is certified that error appears in the above-identified patent and that said Letters Patent are hereby corrected as shown below:

Column 4, line 45; column 7, line 35, in formula (VIII) the side chain at $C_{17}$ should appear as follows:

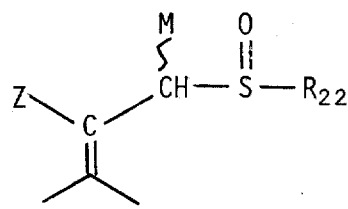

Column 4, line 60; column 6, line 35; and column 8, line 5, in formula (IX) the side chain at $C_{17}$ should appear as follows:

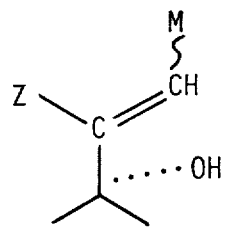

Column 6, line 43, the "A" should be an --M--.

UNITED STATES PATENT OFFICE
CERTIFICATE OF CORRECTION

Patent No. 4,401,599             Dated August 30, 1983

Inventor(s) Jerry A. Walker

It is certified that error appears in the above-identified patent and that said Letters Patent are hereby corrected as shown below:

Column 2, line 24, "R"$_3$" should read --R$_3$"--.
Column 2, lines 42-44, "R'$_3$ and R"$_3$" should read --R$_3$' and R$_3$"--.
Column 3, lines 23-25, "R'$_3$ and R"$_3$" should read --R$_3$' and R$_3$"--.
Column 3, lines 48-50, "R'$_3$ and R"$_3$" should read --R$_3$' and R$_3$"--.
Column 4, lines 27-30, should appear as follows instead of as in the patent:

Column 5, line 20, "phthalamide" should read --phthalimide--.
Column 6, line 44, "claim 7" should read --claim 1--.
Column 6, line 3, "malolate" should read --malonate--.
Column 7, lines 6-7, should appear as follows instead of as in the
    patent:  A
             ‖
             CH Signed and Sealed this Second Day of October 1984

[SEAL]

Attest:

GERALD J. MOSSINGHOFF

Attesting Officer    Commissioner of Patents and Trademarks